(12) United States Patent
Shen

(10) Patent No.: US 10,562,698 B2
(45) Date of Patent: Feb. 18, 2020

(54) PACKAGE FOR DISPOSABLE COATED ACUPUNCTURE NEEDLE

(71) Applicant: Yimin Shen, Qingdao (CN)

(72) Inventor: Yimin Shen, Qingdao (CN)

( * ) Notice: Subject to any disclaimer, the term of this patent is extended or adjusted under 35 U.S.C. 154(b) by 0 days.

(21) Appl. No.: 15/241,068

(22) Filed: Aug. 19, 2016

(65) Prior Publication Data

US 2016/0355324 A1 Dec. 8, 2016
US 2017/0267443 A9 Sep. 21, 2017

Related U.S. Application Data

(63) Continuation-in-part of application No. PCT/CN2015/000111, filed on Feb. 25, 2015.

(30) Foreign Application Priority Data

Feb. 20, 2014 (CN) .......................... 2014 1 0064777

(51) Int. Cl.
| | |
|---|---|
| *B65D 85/24* | (2006.01) |
| *A61H 39/08* | (2006.01) |
| *A61B 50/33* | (2016.01) |
| *A61B 50/30* | (2016.01) |
| *A61B 50/20* | (2016.01) |
| *B65D 83/02* | (2006.01) |
| *A61B 50/00* | (2016.01) |

(52) U.S. Cl.
CPC .............. *B65D 85/24* (2013.01); *A61B 50/20* (2016.02); *A61B 50/30* (2016.02); *A61B 50/33* (2016.02); *A61H 39/086* (2013.01); *B65D 83/02* (2013.01); *A61B 2050/0057* (2016.02); *A61B 2050/3008* (2016.02)

(58) Field of Classification Search
CPC ...... B65D 85/24; B65D 83/02; A61H 39/086; A61B 50/20; A61B 50/30; A61B 50/33
USPC .... 206/380, 45.2, 45.24, 477, 478, 485, 486
See application file for complete search history.

(56) References Cited

U.S. PATENT DOCUMENTS

| | | | |
|---|---|---|---|
| 1,720,274 A * | 7/1929 | Holden | ................... B65D 51/24 206/270 |
| 2,338,425 A * | 1/1944 | Goldbert | ................. A24F 15/16 206/256 |
| 3,315,802 A * | 4/1967 | Ronnow | .......... A61B 17/06133 206/205 |

(Continued)

*Primary Examiner* — Chun Hoi Cheung
(74) *Attorney, Agent, or Firm* — Andrew C. Cheng

(57) ABSTRACT

A package holding acupuncture needles comprises a packaging tray having a needle supporting board with positioning groves defined thereon for securely supporting and positioning acupuncture needles therein; a moveable headrest pivotably attached to an end of the packaging tray; a plurality of acupuncture needles each including an elongate needle body securely received in the corresponding groove, and having a shank extending into the moveable headrest, each of the acupuncture needles including a collapsible film jacket enveloped on the elongate needle body; a sealing bag enveloping the packaging tray and the moveable headrest with the acupuncture needles thereon; and when the sealing bag is removed from the packaging tray, the moveable headrest can be rotated between a horizontal position and a substantial vertical position to support the packaging tray in a way that the shanks of the acupuncture are exposed for being readily retrieved from the packaging tray.

2 Claims, 11 Drawing Sheets

(56) References Cited

U.S. PATENT DOCUMENTS

| | | | | |
|---|---|---|---|---|
| 3,768,635 | A | * | 10/1973 | Eggert .................. A61M 5/002 206/366 |
| 4,163,493 | A | * | 8/1979 | Current .................. B65D 85/24 206/380 |
| 4,573,569 | A | * | 3/1986 | Parker .................... B44D 3/123 206/1.7 |
| 4,657,138 | A | * | 4/1987 | Watson ................. A61M 5/003 206/366 |
| 5,460,267 | A | * | 10/1995 | Schiffer ................. B65D 85/24 206/380 |
| 6,213,296 | B1 | * | 4/2001 | Streich .................... A45C 5/00 206/373 |
| 6,364,100 | B1 | * | 4/2002 | Leibeck ................. A45C 11/24 206/443 |
| D726,819 | S | * | 4/2015 | Botha ........................... D19/75 |
| 2002/0112978 | A1 | * | 8/2002 | Hoch .................... B65D 85/24 206/380 |
| 2006/0102502 | A1 | * | 5/2006 | Biscotti ................. B65D 85/24 206/363 |
| 2009/0288977 | A1 | * | 11/2009 | Vanderbush .......... A61M 5/002 206/524.8 |
| 2010/0042137 | A1 | * | 2/2010 | Oronsky ............. A61H 39/083 606/204 |
| 2010/0089784 | A1 | * | 4/2010 | Kanda ................... A61H 39/08 206/439 |

\* cited by examiner

PACKAGE FOR DISPOSABLE COATED ACUPUNCTURE NEEDLE

CROSS-REFERENCE TO RELATED APPLICATIONS

This application is a continuation in part of International Patent Application No. PCT/CN2015/000111 with a filing date of Feb. 25, 2015, designating the United States, now pending, and further claims priority to Chinese Patent Application No. 201410064777.4 with a filing date of Feb. 20, 2014. The content of the aforementioned applications, including any intervening amendments thereto, are incorporated herein by reference.

TECHNICAL FIELD

The present invention relates to a sterile acupuncture needle package technology, in particular to a package holding disposable acupuncture needles each with a collapsible film jacket.

BACKGROUND OF THE PRESENT INVENTION

In prior art, the package technology of sterile acupuncture needle is that the acupuncture needle is packaged in plastic bubble cap with special dialyzing paper or aluminum foil and sterilization is conducted via high-energy electron or isotope or high-energy electron. If acupuncture needles are packaged in the plastic bubble cap separately, when in use, it should be unsealed separately, the efficiency is low and it is inconvenient when taken out for use; or if multiple acupuncture needles are packaged in the same plastic bubble cap and unsealed, times can be reduced; however, the other needles may be contaminated by fingers when one is taken out for use, and the sterile operation is not facilitated.

SUMMARY OF PRESENT INVENTION

For above problems, the present invention proposes a package holding disposable acupuncture needles. The package holding acupuncture needles comprises: a packaging tray having a needle supporting board with positioning groves defined thereon for securely supporting and positioning acupuncture needles therein; a moveable headrest pivotably attached to an end of the packaging tray; a plurality of acupuncture needles each including an elongate needle body securely received in the corresponding groove, and having a shank extending into the moveable headrest, each of the acupuncture needles including a collapsible film jacket enveloped on the elongate needle body; a sealing bag enveloping the packaging tray and the moveable headrest with the acupuncture needles thereon; and wherein when the sealing bag is removed from the packaging tray, the moveable headrest can be rotated between a horizontal position, in which the shanks of the acupuncture needles are properly protected, and a substantial vertical position, in which the moveable headrest serves as a leg to support the packaging tray in a way that the shanks of the acupuncture are exposed for being readily retrieved from the packaging tray.

The packaging tray is generally made of polyethylene, polypropylene or other suitable medical packaging plastics; the sealing bag is generally made of metal foil, plastic or Al compound packing film; the packaging tray is provided with a groove or a snap joint or an embedded shaft and a supporting connecting device; the packaging tray is embedded with the needle supporting board via the groove or the snap joint, or the packaging tray is embedded with an embedded hole on the needle supporting board via the embedded shaft; a needle embedding device is arranged on the needle supporting board; the shank is simply fixed by the needle embedding device in the form of an embedded clamp or the positioning grooves; the moveable headrest is provided with a box body connecting device; the packaging tray and the moveable headrest are connected in the combination mode of shaft and hole through the support connecting device and the box body connecting device; the moveable headrest can also expose the shank via transposition, and support the packaging tray for conducting sterile operation; the sealing place of one end of the sealing bag is provided with a Y-shaped or V-shaped unsealing notch; the unsealing notch end of the packaging tray is provided with a drawing strap, when the unsealing notch is torn off, the exposed drawing strap is pulled, such that the packaging tray in the sealing bag can be pulled out conveniently, and the location of above pair holes and shafts can be exchanged.

A vacuum packaging technology may be used in the package to seal the packaging box holding the acupuncture needles, so as to perform sterilization via high-energy electron or isotope irradiation. When in use, the sealing bag is torn off, a drawing strap is pulled so as to pull out the package box, the moveable headrest is folded to expose the shank, and then the disposable acupuncture needles can be used for conducting sterile operation.

The present invention has the advantages:

1. Multiple acupuncture needles can be packaged in the same package box and can be conveniently taken for use; a user can less contaminate the other needles when taking and using a small number of acupuncture needles in the package box, and the sterile operation is facilitated.

2. the acupuncture needles with collapsible film jackets are embedded on the needle supporting board, and the sealing bag made up of plastic film or plastic composite film is used as vacuum packaging, such that it has isolation effect as general sealed package, and the whole acupuncture needles with collapsible film jackets can be evenly, smoothly and properly packaged and fixed, which can avoid displacement and disorder of product in transportation process due to improper packaging, and avoid the sharp point of a needle becoming blunt or curving due to collision.

3. the packaging tray and the moveable headrest are connected via the support connecting device, such that the moveable headrest can constitute the structure of the packaging tray with the packaging tray by transposition; the moveable headrest can also expose the shank via transposition, and support the packaging tray for conducting sterile operation, which can increase the technical level and efficiency of sterile operation.

In which: (1): disposable acupuncture needles; (1a): elongate needle body; (1b); collapsible film jacket; (2); packaging box; (3); sealing bag; (4); packaging tray; (5); needle supporting board; (6); moveable headrest; (7); groove; (8); snap joint; (9); support connecting device; (10); needle embedding device; (11); embedding clamp; (12); positioning groove; (13); shank; (14); box body connecting device; (15); unsealing notch; (16); drawing strap; (17); embedding shaft; and (18); embedding hole.

DETAILED DESCRIPTION OF PREFERRED EMBODIMENTS

The present invention is further described with reference to drawings and embodiments.

Figure 1:
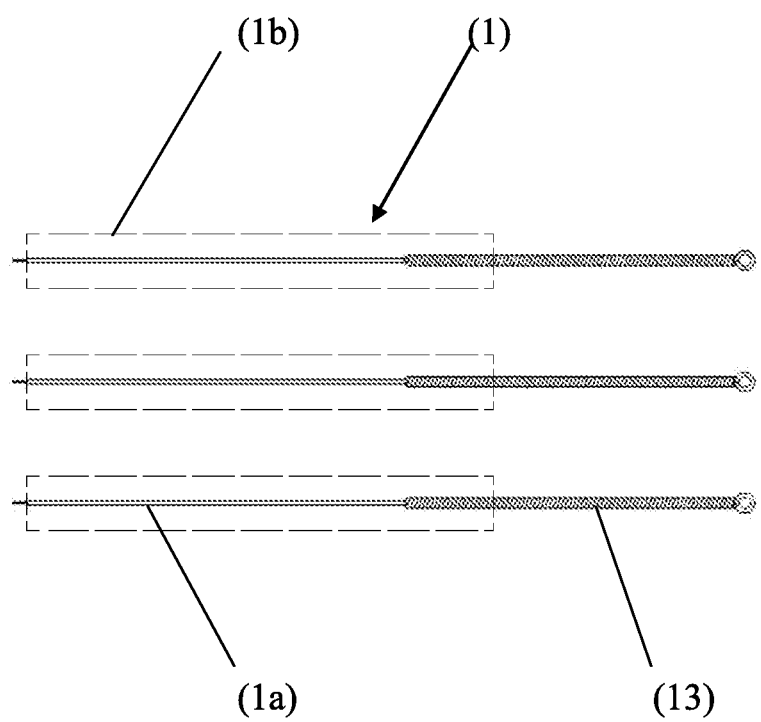
FIG. 1 is a structural schematic diagram of disposable acupuncture needles each with a collapsible film jacket.

FIG. 1 is a structural schematic diagram of disposable acupuncture needles. As shown in FIG. 1, each of the acupuncture needles includes an elongate needle body 1a, a shank 13 and a collapsible film jacket 1b enveloped on the elongate needle body 1a.

FIGS. 2 to 12 are packaging structural schematic diagrams according to the embodiments of the present invention. As shown in the figures, a packaging tray 4, a needle supporting board 5 and a moveable headrest 6 are made by injection of polyethylene material, and the shank 13 is embedded on the needle embedding device in the form of an embedding clamp 11. The packaging tray 4 and the moveable headrest 6 are connected, such that the moveable headrest 6 can constitute the structure of a packaging box 2 with the packaging tray 4 by transposition; the moveable headrest 6 can also expose the shank 13 via transposition, and support the packaging tray 4 for conducting sterile operation.

Figure 3:
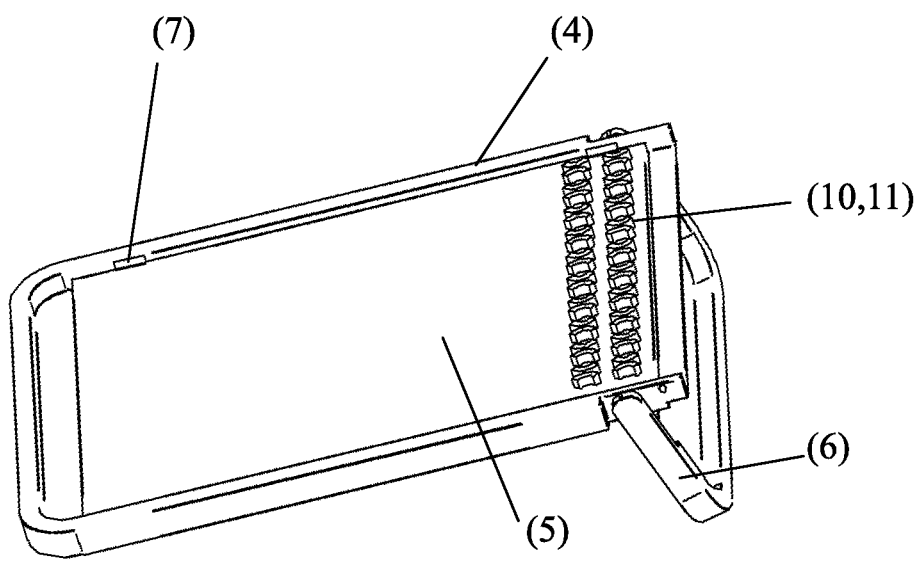
FIG. 3 is another structural schematic diagram of the package according to the disclosure.

FIG. 3 is another packaging structural schematic diagram according to the embodiments of present invention. The packaging tray 4 has the needle supporting board 5 with a needle embedding device 10 defined thereon for securely supporting and positioning the acupuncture needles 1. The embedding device 10 shown in FIG. 3 is an embedding clamp 11. The moveable headrest 6 is pivotably attached to an end of the packaging tray 4. A groove 7 is defined on the packaging tray 4 and the needle supporting board 5 is embedded into the packaging tray 4 via the groove 7.

Figure 4:
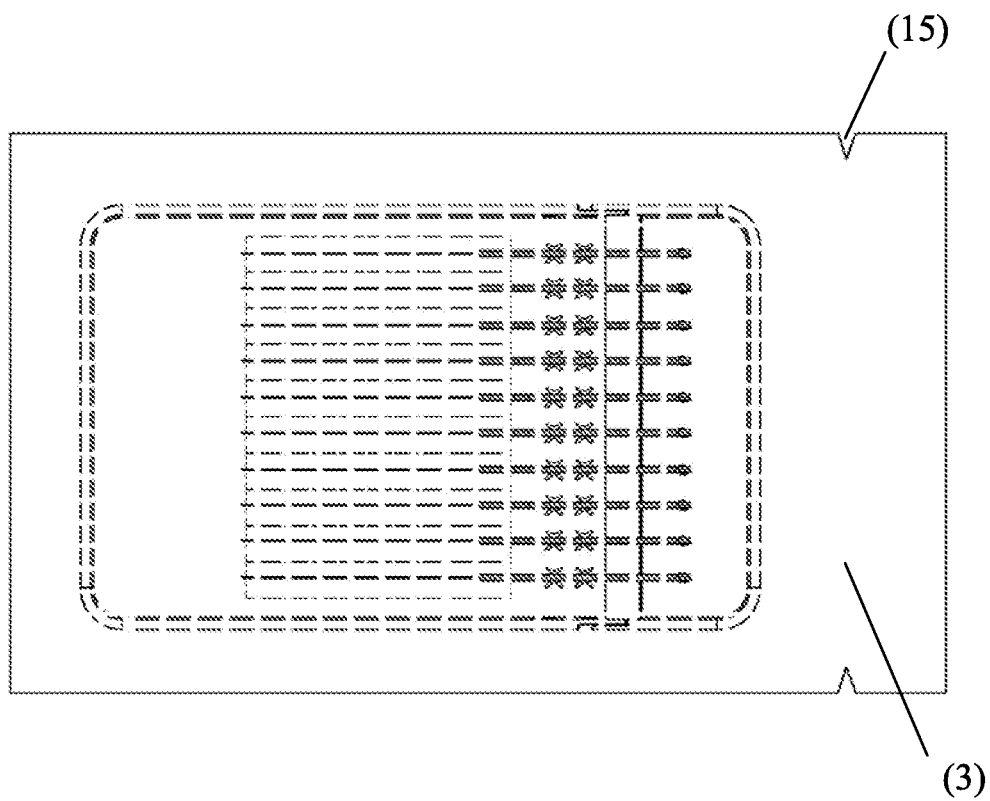
FIG. 4 is a schematic diagram of a sealed bag of the package according to the disclosure.

FIG. 4 is a schematic diagram of a sealing bag used as vacuum packaging. The package further comprises a sealing bag 3 having an unsealing notch 15. As shown in FIG. 4, the sealing bag 3 is generally made of metal foil, plastic or Al compound packing film, when packaging, the sealing bag 3 is vacuumed by vacuum machine. The sealing bag 3 is configured to envelope the packaging tray 4 and the moveable headrest 6 with the acupuncture needles 1 thereon.

Figure 5:
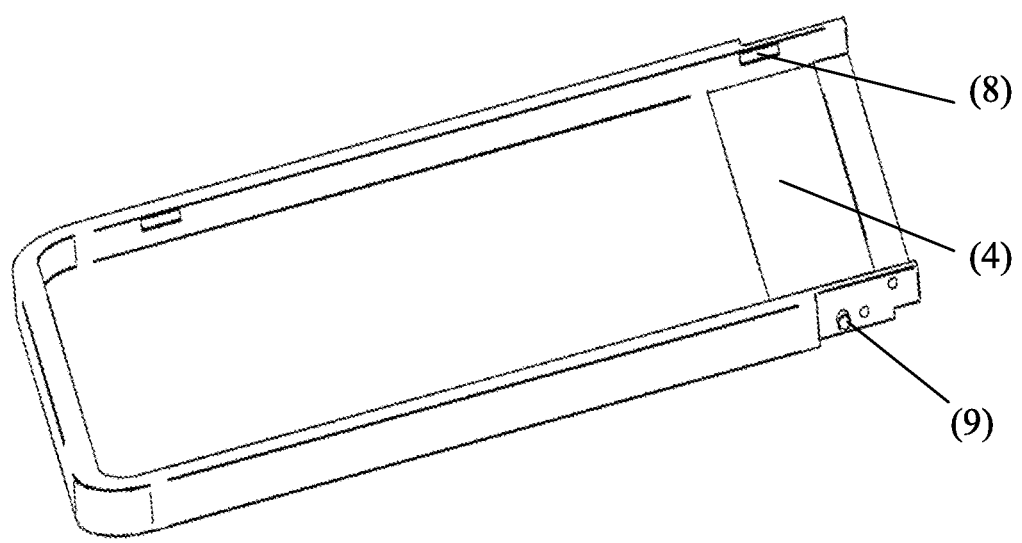
FIG. 5 is a structural schematic diagram of a packaging tray of the package according to the disclosure.
Figure 6:
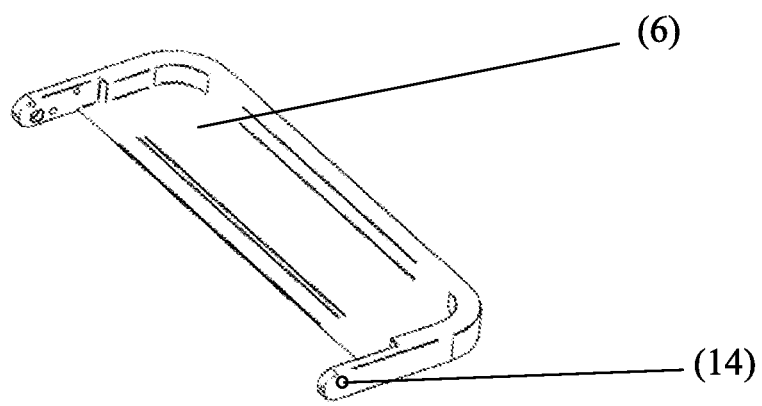
FIG. 6 is a structural schematic diagram of a moveable headrest of the package according to the disclosure.

FIG. 5 and FIG. 6 are structural schematic diagrams of the packaging tray and moveable headrest pivotably attached thereto according to the embodiments of the present invention. The moveable headrest 6 may attached to an end of the packaging tray 4 via a support connecting device (9). A snap joint 8 is defined on the packaging tray 4 and the needle supporting board 5 may also be embedded into the package tray 4 via the snap joint 8. One preferred embodiment of the snap joint 8 is taper or trapezoid, which is convenient for the insertion of the needle supporting board 5. One preferred embodiment of the support connecting device 9 is cylinder, which is for cooperation with the hole of a box body connecting device 14.

Figure 2:
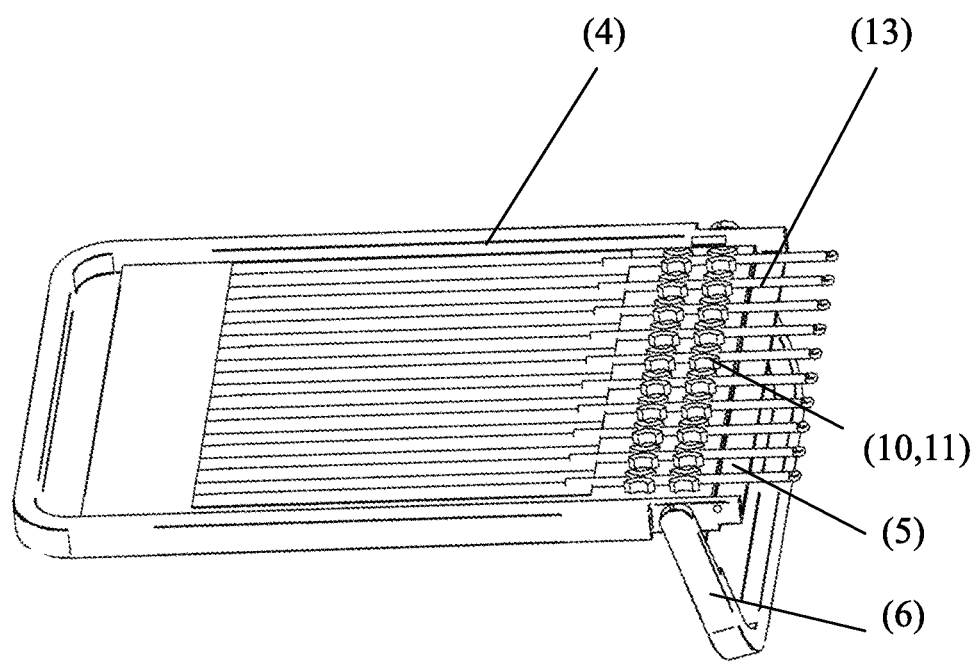
FIG. 2 is a structural schematic diagram of a package holding the disposable acupuncture needles according to the disclosure.

FIG. 2 and FIG. 6 show the moveable headrest according to the embodiments of the present invention. The packaging tray 4 and the moveable headrest 6 are connected in the combination mode of shaft and hole through the support connecting device 9 and the box body connecting device 14, such that the moveable headrest 6 can constitute the structure of the packaging box 2 with the packaging tray 4 by transposition; the moveable headrest 6 can also expose the shank 13 via transposition, and support the packaging tray 4.

Figure 7:
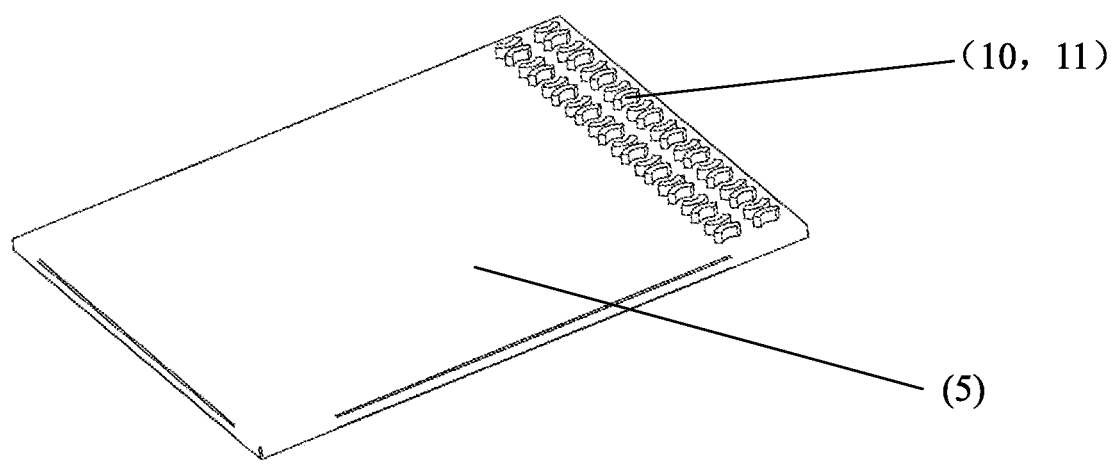
FIG. 7 is a structural schematic diagram of a needle supporting board of the package according to the disclosure.

FIG. 7 is a structural schematic diagram of a needle supporting board according to the embodiments of the present invention. The needle supporting board 5 is provided with the needle embedding device 10, and one preferred embodiment of the needle embedding device 10 is in the form of the embedding clamps 11.

Figure 8:
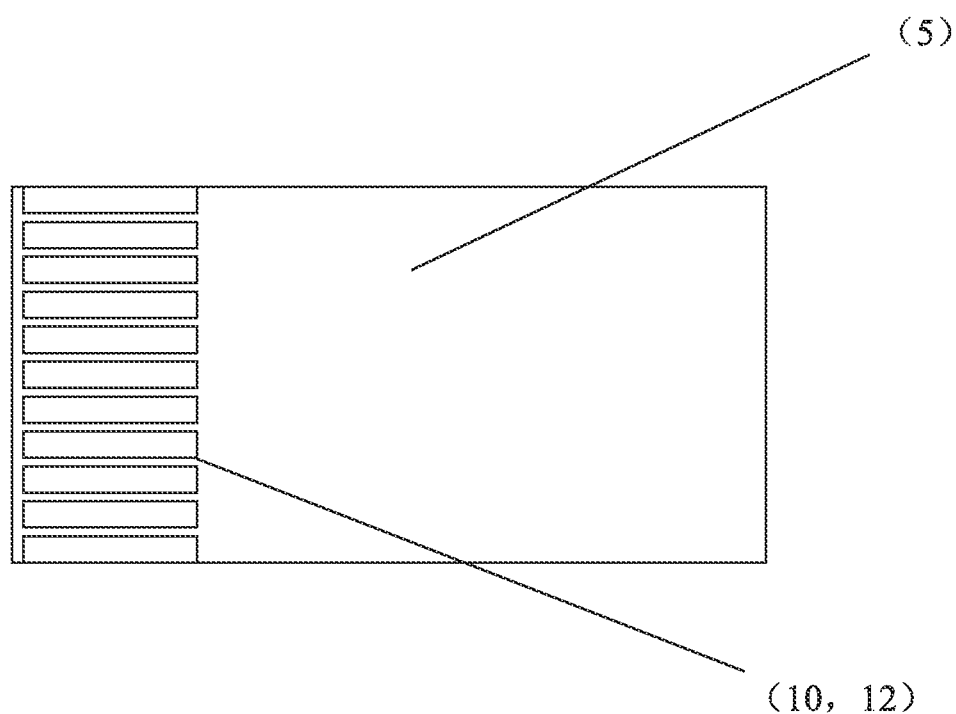
FIG. 8 is another structural schematic diagram of a needle supporting board of the package f according to the disclosure.

FIG. 8 is another structural schematic diagram of a needle supporting board according to the embodiments of the present invention. The needle supporting board 5 is provided with the needle embedding device 10, and the other preferred embodiment of the needle embedding device 10 is in the form of the positioning grooves 12. The positioning groves 12 are defined for securely supporting and positioning the acupuncture needles therein.

Figure 9:
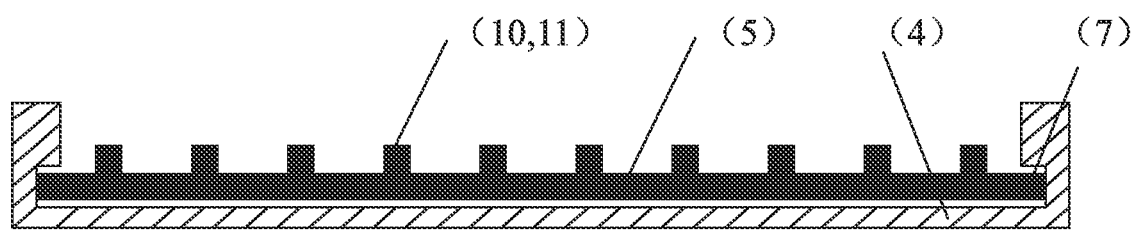
FIG. 9 is a cross-sectional diagram of a packaging box of the package according to the disclosure.

FIG. 9 is a cross-sectional diagram of the package according to the embodiments of the present invention. One preferred embodiment is that the packaging tray 4 is embedded with the needle supporting board 5 via the groove 7.

Figure 10:
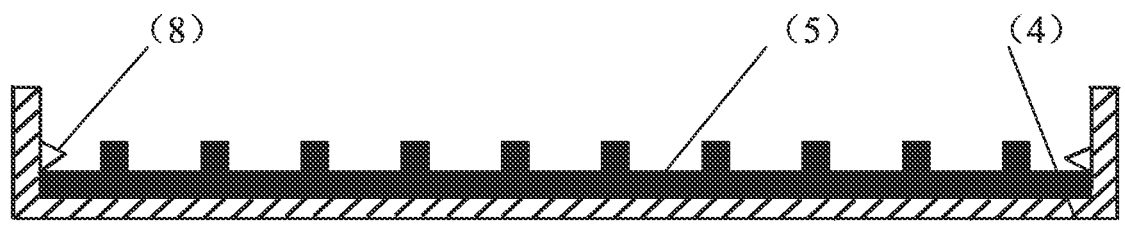
FIG. 10 is the other cross-sectional diagram of a packaging box of the package according to the disclosure.

FIG. 10 is the other cross-sectional diagram of the package according to the embodiments of the present invention. The other preferred embodiment is that the packaging tray 4 is embedded with the needle supporting board 5 via the snap joint 8.

Figure 11:
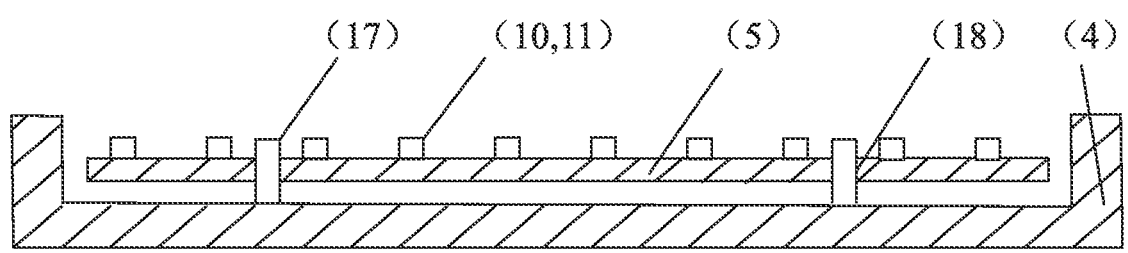
FIG. 11 is another cross-sectional diagram of a packaging box of the package according to the disclosure.

FIG. 11 is another cross-sectional diagram of the package according to the embodiments of the present invention. Another preferred embodiment is that the packaging tray 4 is embedded with an embedded hole 18 on the needle supporting board 5 via the embedded shaft 17.

Figure 12:
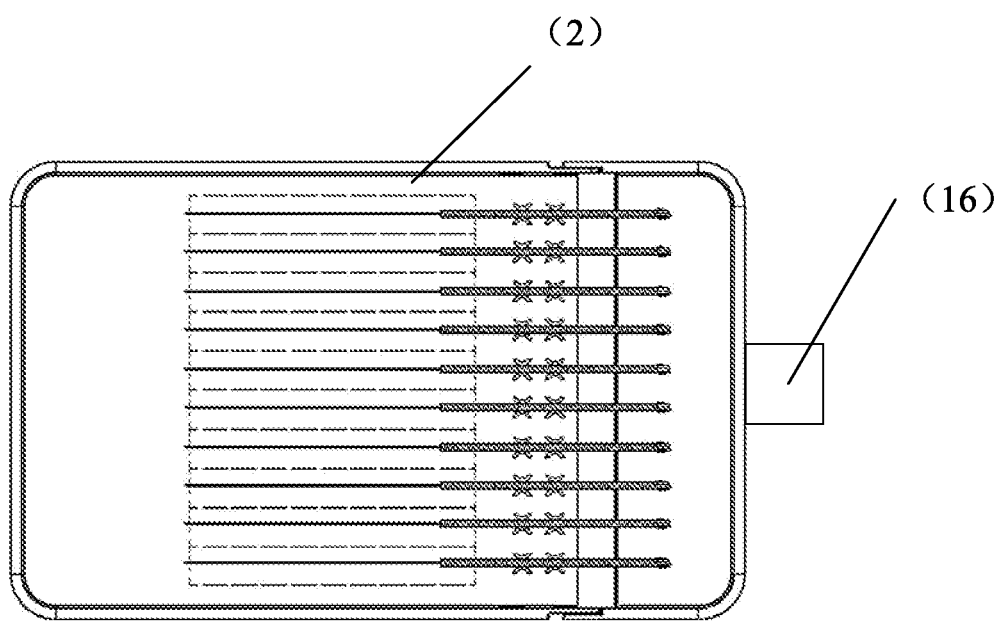
FIG. 12 is a top view of the inner model appearance of the package according to the disclosure.

FIG. 4 and FIG. 12 show a top view of the inner model appearance of the package according to the embodiments of the present invention. The package further comprises a drawing strap 16, and when the unsealing notch 15 is torn off, the exposed drawing strap 16 is pulled, such that the packaging tray 4 in the sealing bag 3 can be pulled out conveniently.

When the sealing bag 3 is removed from the packaging tray 4, the moveable headrest 6 is capable of rotating between a horizontal position, in which the shanks 13 of the acupuncture needles 1 are properly protected, and a substantial vertical position, in which the moveable headrest 6 serves as a leg to support the packaging tray 4 in a way that the shanks 13 of the acupuncture are exposed for being readily retrieved from the packaging tray 4.

The invention claimed is:

1. A package holding acupuncture needles, comprising:

a packaging tray (4) having a needle supporting board (5) with positioning grooves (12) defined thereon for securely supporting and positioning acupuncture needles (1) therein; wherein a groove (7) or a snap joint (8) is defined on the packaging tray (4) and the needle supporting board (5) is embedded into the packaging tray (4) via the groove (7) or the snap joint (8);

a moveable headrest (6) pivotably attached to an end of the packaging tray (4);

a plurality of acupuncture needles (1) each including an elongate needle body securely received in the corresponding positioning groove, and having a shank (13) extending into the moveable headrest (6), each of the acupuncture needles including a collapsible film jacket enveloped on the elongate needle body;

a sealing bag (3) enveloping the packaging tray (4) and the moveable headrest (6) with the acupuncture needles (1) thereon; and wherein when the sealing bag (3) is removed from the packaging tray (4), the moveable headrest (6) is capable of rotating between a horizontal position, in which the shanks (13) of the acupuncture needles (1) are properly protected, and a substantial vertical position, in which the moveable headrest (6) serves as a leg to support the packaging tray (4) in a way that the shanks (13) of the acupuncture needles (1) are exposed for being readily retrieved from the packaging tray (4).

2. A package holding acupuncture needles, comprising a packaging tray having a needle supporting board with positioning grooves defined thereon for securely supporting and positioning acupuncture needles therein;

a moveable headrest pivotably attached to an end of the packaging tray;

a plurality of acupuncture needles each including an elongate needle body securely received in the correspond positioning groove, and having a shank extending into the moveable headrest, each of the acupuncture needles including a collapsible film jacket enveloped on the elongate needle body;

a sealing bag enveloping the packaging tray and the moveable headrest with the acupuncture needles thereon; and wherein when the sealing bag is removed from the packaging tray, the moveable headrest is capable of rotating between a horizontal position, in which the shanks of the acupuncture needles are properly protected, and a substantial vertical position, in which the moveable headrest serves as a lee to support the packaging tray in a way that the shanks of the acupuncture are exposed for being readily retrieved from the packaging tray.

* * * * *